(12) United States Patent
Wu et al.

(10) Patent No.: US 10,479,805 B2
(45) Date of Patent: Nov. 19, 2019

(54) BETA-LACTAMASE INHIBITOR

(71) Applicant: WUHAN VISION PHARMACEUTICAL TECHNOLOGY CO., LTD., Wuhan (CN)

(72) Inventors: Shiping Wu, Wuhan (CN); Hongyu Xu, Wuhan (CN); Xiangdong Hu, Wuhan (CN)

(73) Assignee: WUHAN VISION PHARMACEUTICAL TECHNOLOGY CO., LTD., Wuhan (CN)

( * ) Notice: Subject to any disclaimer, the term of this patent is extended or adjusted under 35 U.S.C. 154(b) by 0 days.

(21) Appl. No.: 16/164,929

(22) Filed: Oct. 19, 2018

(65) Prior Publication Data

US 2019/0048027 A1    Feb. 14, 2019

Related U.S. Application Data

(63) Continuation-in-part of application No. PCT/CN2017/080337, filed on Apr. 13, 2017.

(30) Foreign Application Priority Data

Apr. 19, 2016    (CN) .......................... 2016 1 0243093

(51) Int. Cl.
*C07F 5/02* (2006.01)
*A61P 31/04* (2006.01)
*A61K 31/69* (2006.01)

(52) U.S. Cl.
CPC .............. *C07F 5/025* (2013.01); *A61K 31/69* (2013.01); *A61P 31/04* (2018.01); *C07F 5/02* (2013.01)

(58) Field of Classification Search
None
See application file for complete search history.

(56) References Cited

U.S. PATENT DOCUMENTS

2014/0194385 A1*   7/2014   Reddy .................. A61K 31/407
                                                          514/64

* cited by examiner

*Primary Examiner* — Po-Chih Chen
(74) *Attorney, Agent, or Firm* — Matthias Scholl P.C.; Matthias Scholl

(57) ABSTRACT

A beta-lactamase inhibitor having a formula (I). Also provided is a method of using the beta-lactamase inhibitor for prevention or treatment of diseases.

1 Claim, 7 Drawing Sheets

| Examples | Class A | | | Class B | Class C | Class D |
|---|---|---|---|---|---|---|
| | SHV-5 | CTXM-15 | KPC-2 | VIM-2 | P99+ | OXA-23 |
| 1 | C | C | C | C | C | C |
| 2 | C | C | C | C | C | C |
| Clavulanic acid control group | C | C | A | A | A | A |

FIG. 6

| Examples | Class A | | | Class B | Class C | Class D |
|---|---|---|---|---|---|---|
| | *E. coli* SHV-5 plus CAZ (8 µg/mL) | *E. coli* CTXM-15 plus TAX (8 µg/mL) | *Klebsiella pneumoniae* KPC-2 plus CAZ (8 µg/mL) | *Pseudomonas aeruginosa* VIM-2 plus CAZ (16 µg/mL) | *Enterobacter cloacae* P99+ plus CAZ (8 µg/mL) | *Acinetobacter Bauman* OXA-23 plus CAZ (16 µg/mL) |
| 1 | B | C | C | B | C | B |
| 2 | C | C | C | B | C | B |
| Clavulanic acid | C | C | B | A | A | A |

FIG. 7

BETA-LACTAMASE INHIBITOR

CROSS-REFERENCE TO RELATED APPLICATIONS

This application is a continuation-in-part of International Patent Application No. PCT/CN2017/080377 with an international filing date of Apr. 13, 2017, designating the United States, now pending, and further claims foreign priority benefits to Chinese Patent Application No. 201610243093.X filed Apr. 19, 2016. The contents of all of the aforementioned applications, including any intervening amendments thereto, are incorporated herein by reference.

BACKGROUND

The disclosure relates to a beta-lactamase inhibitor.

Beta-lactamases (β-lactamases) are the primary cause of bacterial resistance to β-lactam antibiotics. The most widely used classification of β-lactamases is the Ambler classification that divides β-lactamases into four classes (A, B, C and D) based upon their amino acid sequence.

Beta-lactamase inhibitors are a class of drugs that block the activity of beta-lactamases, preventing the degradation of beta-lactam antibiotics. They tend to have little antibiotic activity on their own.

Conventional β-lactamase inhibitors include clavulanate, sulbactam, and tazobactam. These inhibitors mainly inhibit the activity of f-lactamases of classes A and C, and exhibit minimal efficacy to the classes B and D.

SUMMARY

The disclosure provides a beta-lactamase inhibitor.
Disclosed is a compound of formula (I):

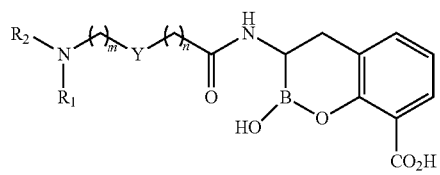

(I)

where: m is 0, 1 or 2;
n is 0 or 1;
Y is —$C_5H_3N$—; and
$R_1$, $R_2$ at each occurrence are hydrogen, amino, —C=NH($NH_2$), hydroxyl, halogen carboxyl, cyano, thiol, substituted $C_1$-$C_5$ alkyl, $C_1$-$C_5$ alkoxy, $C_1$-$C_5$ alkenyl, $C_3$-$C_6$ cycloalkyl, $C_3$-$C_6$ heterocyclic, thioether, or sulfone.

The compound (I) can be:

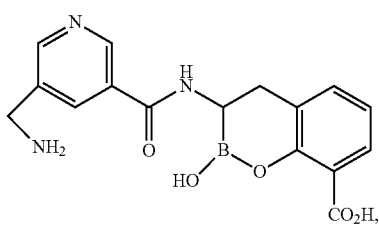

I-1

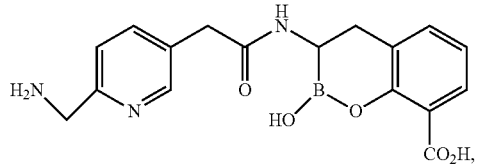

I-2

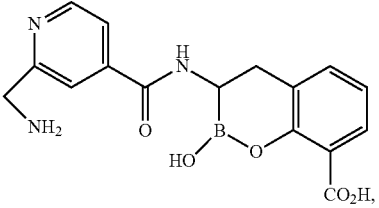

I-3

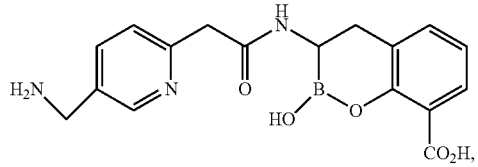

I-4

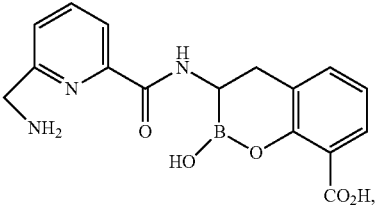

I-5

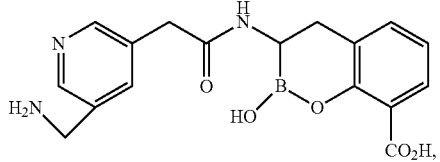

I-6

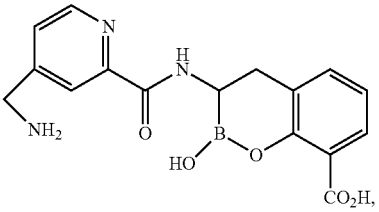

I-7

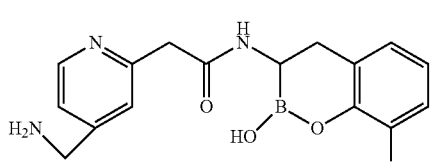

I-8

The compound (I) can be:

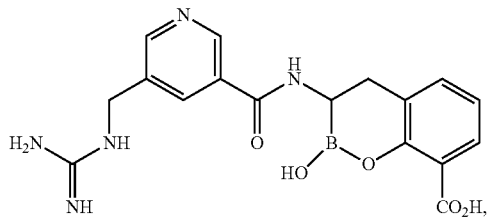

-continued

Further disclosed is a method of preparing a pharmaceutical composition comprising admixing the compound of formula (I) to a drug for prevention or treatment of diseases.

The method can further comprise processing the pharmaceutical composition into a dosage form of injections, powder injections, oral agents, sprays, capsules, suppositories, or pharmaceutically-acceptable excipients.

The drug can comprise a beta-lactam antibiotic.

The method can further comprise adding a pharmaceutically-acceptable carrier to the mixture of the compound and the drug to yield the pharmaceutical composition.

The compound (I) can be synthesized following a synthetic route as shown in FIG. 1.

In the synthesis scheme, first, in the presence of concentrated sulfuric acid, 2-methylpropene is used to convert the carboxylic acid group into tert-butyl ester for protection, and then (+)-2,3-pinanediol is used to convert boric acid into chiral borate ester. The benzyl borate ester is obtained by a conventional homologous reaction of (bromomethyl) lithium. The obtained intermediates can contact an active ester to yield corresponding amides. The active ester can be obtained by reaction of a carboxylic acid with N-hydroxysuccinimide (NHS) and 3-dimethylaminopropyl)-3-ethyl-carbodiimide hydrochloride reagent (EDCI). The removal of pinane diol groups and the deprotection of carboxylic and phenolic groups can be one-step accomplished under acidic conditions, such as in a solution of dichloromethane containing a Lewis acid such as boron trichloride ($BCl_3$) or boron tribromide ($BBr_3$), or aluminum chloride ($AlCl_3$). Relatively small amounts of I-(S) isomers may be produced in the reaction product, and the dominant (more than 99%) is I-(R) enantiomer according to the methods. Also, as shown in the synthesis scheme, these compounds having o-hydroxy groups on the aryl ring may be present as free carboxylic acids, or in the form of cyclic borates, or in a mixture of cyclic and open chain forms.

The Use and Administration of β-Lactamase Inhibitors

When the compound is used in combination with β-lactam antibiotics, it strongly restores the antimicrobial activity of the β-lactam antibiotics against drug-resistant bacteria.

As described above, the compounds of formula (I) have a beta-lactamase inhibitory effect and are therefore used to inhibit beta-lactamases. Specifically, the compounds may be used in combination with antibiotics of other beta lactam antibiotics inactivated by the beta-lactamases to restore the activity of these antibiotics for use in the treatment of infections. Thus, according to one embodiment of the disclosure, there is provided a beta-lactamase inhibitor and a pharmaceutical composition comprising the compound of formula (I) as an active ingredient for use in combination with a beta lactam antibiotic. That is, the beta-lactamase inhibitors and pharmaceutical compositions are administered to animals, including humans, simultaneously or sequentially with beta-lactam antibiotics.

Administration of a beta-lactamase inhibitor may be in any pharmacological form comprising a therapeutically active amount of a beta-lactamase inhibitor or further comprising a pharmaceutically-acceptable carrier or additive such as a stabilizer, surfactant, plasticizer, solubilizer, brightener, thickener, lubricant, buffer, sweetener, Fragrance, fragrance, fragrance, sugar coating agent, flavoring agent, substrate, absorbent, binder, suspending agent, moisturizing agent, coating agent, moisture modifying agent, moisture modifying agent, filler, antifoaming agent, chewing agent, refrigerant, colorant, pH adjusting agent, softening agent, emulsifier, adhesive agent, adhesive agent, foaming agent, A dissolving agent, a liquefying agent, a dissolving accelerator, a dispersing agent of a dissolving accelerator, a dispersing agent, a blasting agent, a disintegrating agent, a disintegrating accelerator, an anti-wetting agent, a sterile agent, a preservative, an analgesic agent, or the like, or a combination of two or more of these additives. The person skilled in the art can select suitable additives for the formulation to prepare the desired form of the pharmaceutical composition according to widely used methods and forms of the pharmaceutical composition. Examples of additives include gelatin, lactose, refined sugar, titanium oxide, starch, corn starch, crystalline cellulose, hydroxypropyl methyl cellulose, carboxymethyl cellulose, hydroxypropyl cellulose, microcrystalline wax, white petrolatum, magnesium aluminum silicate, anhydrous calcium phosphate, magnesium stearate, citric acid, trisodium citrate, sorbitol, fatty acid sorbitol ester, polysorbate (polysorbate), fatty acid sucrose ester, polyoxyethylene hydrogenated castor oil, vegetable oil, polyvinylpyrrolidone, light anhydrous silicic acid, pumice powder, benzyl alcohol, gum arabic, propylene glycol, polyglycol, cyclodextrin and hydroxypropyl cyclodextrin. The dosage regimen may be adjusted, for example the drug may preferably be administered once to several times a day at 0.1 100 mg/kg to 1100 mg/kg (based on the weight of the compound and the route of administration) to provide the best therapeutic response. Therapeutic compositions or pharmaceutical compositions may be administered orally or non-enteric as is known in the art, and examples of orally administered formulations include tablets, granules, granules, powders, powders, syrups, solutions, capsules, chewable tablets or suspensions, and the like. Parenteral routes of administration include intranasal, intraocular, ear, transdermal, endotracheal, rectal, intraurethral, subcutaneous, intramuscular, intravenous, intrathecal or intracerebral administration, etc. Examples of preparations for parenteral administration include injections, drops, inhalers, sprays, suppository, vaginal suppository, transdermal absorbent, transmucosal absorbent, eye drops, ear drops, nasal drops or patches. A liquid formulation, such as an injection or a drop, may provide a pharmaceutical composition, for example in the form of a lyophilized powder, which may be dissolved or suspended in water or other suitable solvent, such as a physiological saline or glucose infusion.

Beta-lactamase inhibitors may also be linked or conjugated with antibodies to transferrin receptors, polyethylene glycols, etc., to achieve the desired solubility, stability, half-life and other pharmaceutically advantageous properties. Beta lactam antibiotics include penicillins, cephalosporins, carbapenems, monocyclic lactams, bridged monocyclic lactams, or their prodrugs and combinations, which may be used in the form of pharmaceutically-acceptable salts, such as sodium salts. Examples of penicillins include penicillin, penicillin V, ampicillin, amoxicillin, amoxicillin, carboxicillin, ampicillin, impicillin, epiracillin, tepicillin, cyclohexicillin, piroxicillin, meloxicillin, sulbacillin, piperacillin and other well-known penicillin. Illustrative example of cephalosporins include cefotaxime, ceftriaxone, ceftriaxone, ceftriaxone, ceftazidime, cefazolin, cefalexin, cefapilil, cefapilin, cefapilin, cefamandolenaphate, cefradine, 4-hydroxycefalexin, cefoperazone, oxafenone, cefminox, fluoxofos, ceftazidime, ceftazidime, cefuroxime, cefotazolam, cefmetazole, cefpiroxil, cefazolin and other well-known cephalosporins are also described herein. Specific examples of carbapenems include imipenem, meropenem, ertapenem, biapenem, doripenem, tebipenem, and the like.

The beta-lactamase inhibitor or a pharmaceutically-acceptable salt thereof may be administered at the same time as the administration of the beta-lactam antibiotic, or separately. This can be carried out in the form of a mixture of two active ingredients or in the form of a pharmaceutical combination product of two independent active ingredients. The strains producing beta-lactamases include, for example, *E. coli, Klebsiella pneumoniae, Pseudomonas aeruginosa, Bacillus cereus, Acinetobacter baumannii, Enterobacter cloacae, Bacteroides fragilis, Aeromonas hydrophila, Serratia mucosae, Stenosus*, Xylose-oxidizing alkali-producing bacilli, *Legionella grammoni pneumonia, meningeal pyogenic chrysobacteria*, indole-producing *chrysogenum bacilli* and *phloem citrate bacilli*, and the like. The dosage of beta-lactamase inhibitors and their pharmaceutically-acceptable salts and their ratio to beta-lactam antibiotics can also vary widely, for example in a weight ratio of 1:0.5 to 1:18. It should be understood that the amount of composition actually administered will be determined by the physician according to the relevant circumstances, including the disease to be treated; the selection of the composition to be administered; age, body weight and response of individual patients; the severity of the patient's symptoms and the route of administration chosen.

The disclosure also provides a method of inhibiting bacterial growth by, for example, reducing bacterial resistance to beta lactam antibiotics. The method comprises contacting a bacterial cell culture with a beta-lactamase inhibitor as described herein. Bacteria that are inhibited by administration of the beta-lactamase inhibitors are bacteria that are resistant or highly resistant to beta-lactam antibiotics. Experiments to inhibit beta-lactamase activity are well known in the art. For example, standard enzyme inhibition assays that determine the ability of a compound to inhibit beta-lactamase activity may be employed. The beta-lactamases used in such experiments may be prepared from recombinant DNA techniques, may also be purified from bacterial sources, or the sensitivity of known or engineered beta-lactamase producing bacteria to inhibitors may be determined. Other experiments on bacterial inhibition include agar plate diffusion and agar dilution. Beta-lactamases can thus be inhibited by contacting the beta-lactamase with an effective amount of the compound of the invention, or by contacting the bacteria producing the beta-lactamase with an effective amount of said compound, thereby bringing the beta-lactamase in the bacteria into contact with the inhibitor. Contact can occur in vitro or in vivo, enabling the inhibitor to bind to beta-lactamases. Inhibition includes reduction and elimination of beta-lactamase activity.

Advantages of the compound according to embodiments of the disclosure are summarized as follows.

The compounds show effective activity against four classes (A, B, C and D) of beta-lactamases.

Through the study of the activity of the compound against four types of β-lactamases, it is found that the compound can successfully inhibit the activity of four types of β-lactamases (SHV-5, CTXM-15, KPC-2, VIM-2, P99+, OXA-23), Moreover, when they are combined with β-lactam antibiotics, they have strong growth inhibitory activity against various kinds of bacteria producing β3-lactamases, and can be expected to develop into a drug which can restore the antibacterial activity of β-lactam antibiotics to treat and prevent infections caused by bacteria in animals, including human beings.

BRIEF DESCRIPTION OF THE DRAWINGS

FIG. 6 shows half inhibitory concentration IC50 (μM) for various β-lactamase activities of the compounds as descried in the disclosure; and FIG. 7 shows MIC of bacterial growth inhibition of compounds as descried in the disclosure in combination with cephalosporin antibiotics.

DETAILED DESCRIPTION

To further illustrate, examples detailing a compound of beta-lactamase inhibitors are described below. It should be noted that the following examples are intended to describe and not to limit the description.

Figure 1:
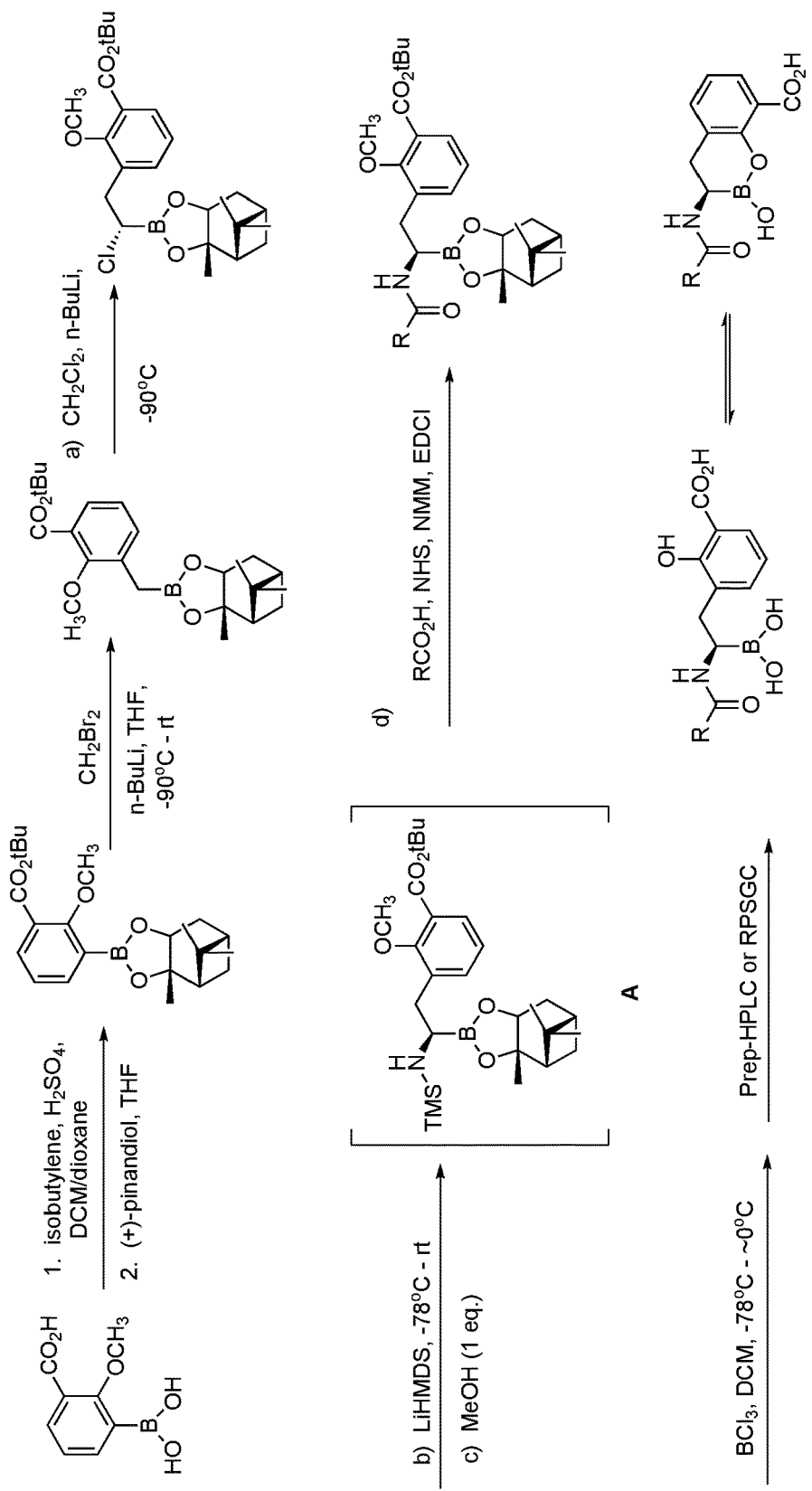
FIG. 1 is a synthetic route of a compound (I) as described in the disclosure.

The beta-lactamase inhibitor having a formula (I) is synthesized following the synthetic route as shown in FIG. 1.

In the synthesis scheme, first, in the presence of concentrated sulfuric acid, 2-methylpropene is used to convert the carboxylic acid group into tert-butyl ester for protection, and then (+)-2,3-pinanediol is used to convert boric acid into chiral borate ester. The benzyl borate ester is obtained by a conventional homologous reaction of (bromomethyl) lithium. The obtained intermediates can contact an active ester to yield corresponding amides. The active ester can be obtained by reaction of a carboxylic acid with N-hydroxysuccinimide (NHS) and 3-dimethylaminopropyl)-3-ethylcarbodiimide hydrochloride reagent (EDCI). The removal of pinane diol groups and the deprotection of carboxylic and phenolic groups can be one-step accomplished under acidic conditions, such as in a solution of dichloromethane containing a Lewis acid such as boron trichloride ($BCl_3$) or boron tribromide ($BBr_3$), or aluminum chloride ($AlCl_3$). Relatively small amounts of I-(S) isomers may be produced in the reaction product, and the dominant (more than 99%) is I-(R) enantiomer according to the methods. Also, as shown in the synthesis scheme, these compounds having o-hydroxy groups on the aryl ring may be present as free carboxylic acids, or in the form of cyclic borates, or in a mixture of cyclic and open chain forms.

Example 1

Synthesis of Compound I-1

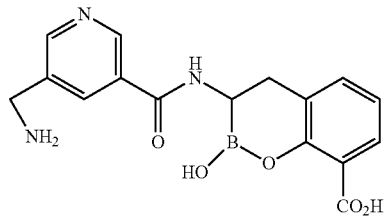

I-1

The compound I-1 is a specific structure of the formula (I) when m=1, n=0, Y is 3,5-disubstituted-$C_5H_3N$, R1 and R2 are hydrogen.

Figure 2:
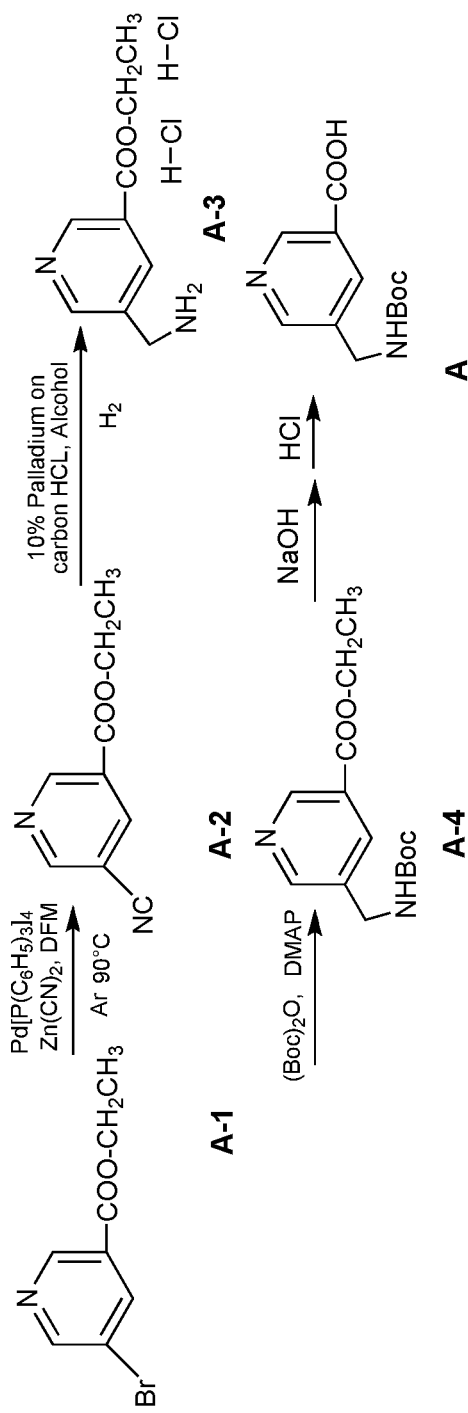
FIG. 2 is a synthetic route of a compound A as described in the disclosure.

I. Synthesis of (2-tert-butoxycarbonyl)-5-aminomethylpyridine-3-carboxylic acid, i.e. Compound A, and the Synthetic Route is Shown in FIG. 2

Step 1. Synthesis of ethyl 5-cyanotinate (Compound A-2)

Ethyl 5-bromonicotinate (Compound A-1, 4.60 g, 20.0 mmol), zinc cyanide (9.94 g, 84.6 mmol), tetrad (triphenylphosphine) (4.69 g, 4.06 mmol), and DMF (100 mL) were added to a 300 mL round bottom flask. The mixture was heated at 90° C. under argon for 15 hours. After cooling, the reaction was quenched with 10% ammonium acetate solution and extracted with ethyl acetate. The combined organic extracts were washed with water, brine and concentrated. The residue was purified by silica gel chromatography eluting with a gradient of 2/98 (v/v, volume to volume ratio) ethyl acetate/hexane to 10/90 (v/v) ethyl acetate/hexane to give product A-2: 3.36 g (92%). ESI-MS M/Z 177 $(MH)^+$.

Step 2. Synthesis of 5-aminomethyl-ethyl nicotinate dihydrochloride (Compound A-3)

Ethyl 5-cyanotinate (Compound A-2, 3.88 g, 22.0 mmol), a solution of 10% palladium on carbon (2 g) and hydrochloric acid (15.7 mL, 4M in dioxane) were dissolved in ethanol (140 mL) and charged with 60 psi hydrogen and stirred in a Parr shaker for 4 hours. The mixture was filtered through Celite and the filtrate was concentrated to give 5.10 g of crude product (92%) Compound A-3. ESI-MS M/Z 181 $(MH)^+$.

Step 3. Synthesis of 5-tert-butoxycarbonyl aminomethyl-ethyl nicotinate (Compound A-4)

5-aminomethyl-ethyl nicotinate dihydrochloride (Compound A-3.5.08 g, 20.0 mmol), di-tert-butyl dicarbonate (13.05 g, 60.0 mmol), sodium bicarbonate (3.36 g, 40.0 mmol), and 4-(dimethylamino) pyridine (DMAP 5.10 mg, 4.15 mmol) were added to a solution of 40 mL of unbutanol and 13 mL of acetone. The mixture was stirred overnight at room temperature. The reaction was quenched with saturated ammonium chloride and extracted three times with ethyl acetate. The combined organic extracts were washed with brine, dried and evaporated. The crude material was purified by silica gel chromatography, eluting from a gradient of 20/80 (V/V) ethyl acetate/hexane to 50/50 (V/V)

ethyl acetate/hexane to give the product 5.60 g (100%) of Compound A-4 as a white solid: ESI-MS RN/Z 281 (MH)+.

Step 4. Synthesis of 5-tert-butoxycarbonyl aminomethyl-nicotinic acid (Compound A)

5-tert-butoxycarbonyl aminomethyl-nicotinic acid ethyl ester (Compound A-4, 5.6 g, 20 mmol) was dissolved in a mixed solution of methanol (20 mL) and water (10 mL), and then sodium hydroxide (10.5 g, 262 mmol) was added. The mixture was stirred at room temperature for 15 hours. The solvent was removed in vacuo and 3N hydrochloric acid was added dropwise with stirring and the pH adjusted to between 4 and 5. The solvent was removed in vacuo and the product purified by C18 reverse phase silica gel chromatography to give 5.56 g (100%) of compound A as a white solid. ESI-MS M/Z 253 (MH)+.

Figure 3:
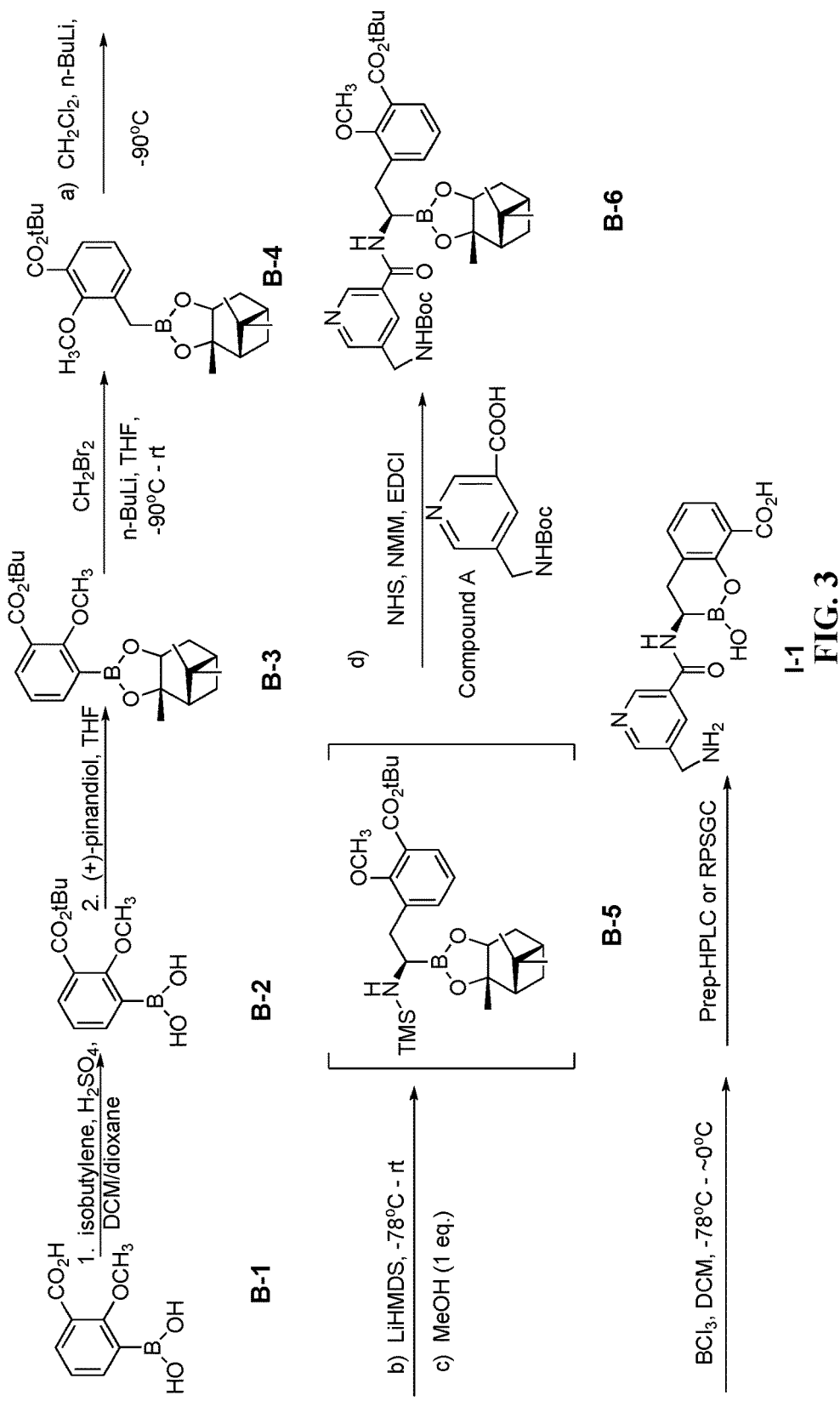
FIG. 3 is a synthetic route of a compound I-1 as described in the disclosure.

II. The Synthetic Route of Compound I-1 is Shown in FIG. 3

Step 1. Synthesis of tert-butyl 3-dihydroxyboro-2-methoxybenzoate (Compound B-2)

3-dihydroxyboro-2-methoxybenzoic acid (Compound B-1, 5.0 g, 25.5 mmol) was added to 1,4-dioxane (30 mL) and sealed in a tube. Additional concentrated sulfuric acid (98%, 15 mL) was added. The solution was cooled to 0° C. and an equal volume of isobutylene was bubbled in. The tube was sealed and stirred at room temperature for 18 hours. The solution was cooled in an ice bath, the seal was opened, and the solution was stirred at room temperature for 30 minutes. The solution was basified with saturated aqueous sodium bicarbonate solution. And extracted twice with ethyl acetate. The combined organic layers were washed with water (5 times), brine, dried over sodium sulfate and concentrated in vacuo to give the product 4.0 g (62%) of white solid compound B-2. ESI-MS M/Z 275 (M+Na)+.

Step 2. Synthesis of 2-methoxy-3-(2,9,9-trimethyl-3,5-dioxo-4-boro-tricyclic $(6,1,1,0^{2,\,6})$ decyl-4-benzoic acid-tert-butyl ester (Compound B-3)

(+)-2,3-pinanediol (2.70 g, 15.9 mmol) and tert-butyl 3-dihydroxyboryl-2-methoxybenzoate (compound B-2, 4.0 g, 15.9 mmol) dissolved in tetrahydrofuran (THF, 21 mL) were mixed and stirred at room temperature for 15 h. The solution was concentrated in vacuo and the residue was washed with hexane to obtain 5.0 g (86%) of a slowly crystallized white solid, ESI-MS M/Z 409 (M+Na)+.

Step 3. Synthesis of 2-methoxy-3-(2,9,9-trimethyl-3,5-dioxo-4-boro-tricyclic $(6,1,1,0^{2,\,6})$ decyl-4-yl-benzoic acid)-tert-butyl ester (Compound B-4)

Liquid nitrogen at −90° C., 2-methoxy-3-(2,9,9-trimethyl-3,5-dioxo-4-boro-tricyclic $(6,1,1,0^{2,\,6})$ decyl-4-yl) benzoate (compound B-3, 8.5 g, 22 mmol), and dibromomethane (4.96 g, 26.4 mmol) dissolved in THF (65 mL) were added to n-butyllithium (10.56 mL, 2.5 M in hexane, 26.4 mmol) was added over 10 minutes. The solution was stirred at −90° C. for 45 minutes. The reaction was gradually warmed and stirred overnight. The reaction was quenched with water and extracted with ethyl acetate. The combined organic layers were washed with water and brine, dried over magnesium sulfate and concentrated in vacuo. The residue was purified by silica chromatography eluting with a 70% dichloromethane/hexane-30% hexane gradient to obtain 8 g of product compound B-4 (91% yield) as a colorless oil. ESI-MS M/Z 401 (MH)+.

Step 4. Synthesis of 3-(2R)-2-((5-tert-butoxycarbonyl methyl-nicotine)-amino)-2-2,9,9-trimethyl-3,5-dioxo-4-borazine-tricyclic $(6,1,1,0^{2,\,6})$ decyl-4-yl-ethyl-benzoic acid)-tert-butyl ester (Compound B-6)

N-BuLi (10.5 mL, 26.3 mmol, dissolved in 2.5 M hexane solution) was added to a solution of tetrahydrofuran (65 mL) and anhydrous methylene chloride (1.80 mL, 28.50 mmol) at −90° C. within 10 minutes. The solution was stirred at −90° C. and 2-methoxy-3-(2,9,9-trimethyl-4,5-dioxo-4-boro-tricyclic $(6,1,1,0^{2,\,6})$-decyl-4-yl-methyl-isoteryl benzoate (compound B-4, 8.77 g, 21.93 mmol) dissolved in THF (11 mL) was added by syringe within 20 minutes. After 30 minutes, the cold trap was removed and the mixture warmed to 0° C. and kept stirring for 1 hour. The solution was then cooled to −78° C. and lithium bis (trimethylsilyl) amino (LHMDS, 1.0 M THF solution, 24.1 mL) was added within 5 minutes. The reaction was gradually warmed and stirred overnight. The mixture was then cooled to −10° C. and anhydrous methanol (0.96 mL 24.1 mmol) was added, stirred for 45 minutes and then the ice bath was removed and the solution stirred for 1.25 h at room temperature. At this stage LCMS show 2-methoxy-3-(2-(2,9,9-trimethyl-3-5-dioxo-4-boro-tricyclic $(6,1,1,0^{2,\,6})$) decyl to -4-butyl-2-(trimethylsilyl-5-amino)-ester (compound B-5) was produced. The solvent was removed in vacuo and the residue was dissolved in 140 mL of DCM for use.

The prepared (5-tert-butoxycarbonyl aminomethylnicotinic acid (compound A, 5.53 g, 21.93 mmol)) was dissolved in dichloromethane (220 mL) in a separate dry round bottom flask. The solution flask was cooled to 0° C. and NMM (7.3 mL, 66.4 mmol), N-hydroxysuccinimide (NHS) (5.09, 44.2 mmol): 1-(3-dimethylaminopropyl)-3-ethylcarbodiimide hydrochloride (EDCI) was added. And 44.2 millimoles (mmol). The mixture was stirred at 0° C. for 30 minutes and then at room temperature for one hour. To this reaction mixture, a DCM solution of compound B-5 was added at 0° C. The cooling bath was removed and the reaction was quenched with water after stirring at room temperature for 1.5 hours. The aqueous phases were extracted with dichloromethane, and the combined organic layers were dried over sodium sulfate and concentrated in vacuo. The crude product was purified by flash column chromatography of silica gel eluting with a gradient of 30/70 (v/v) ethyl acetate/hexane to 70/30 (v/v) ethyl acetate/hexane to yield 4.36 g (30%) of compound B-6, slightly yellow. ESI-MS M/Z 664 (MH)+.

Step 5. Synthesis of (R)-3-(5-aminomethyl) nicotinamide-2-hydroxy-3,4-dihydro-2H-benzo-(1,2)-dioxaborane-8-carboxylic acid hydrochloride (Compound I-1)

(2-(2-tert-butyrylpyridyl-9-carbox-methyl-3,5-dioxa-4-boron-tricyclic $(6,1,1,0^{2,6})$-decyl-4-yl)-ethyl-2-methoxy-benzoic acid tert-butyl (compound B-6, 4.30 g, 6.48 mmol) was dissolved in dichloromethane (15 mL). Under argon, a solution of boron trichloride (65 mL, 65 mmol, 1M solution in dichloromethane) at −78° C. was added. After stirring the mixture at −78° C. for 1 hour, LC-MS indicated consumption of the starting material at which time the reaction was quenched with water (30 mL) at 0° C. The methylene chloride layer was evaporated. 30 mL of water was added and the aqueous layer was extracted with ether (3 times, 30 mL). The aqueous phase was concentrated, purified by chromatography on C18 reverse phase silica gel to give 1.40 g (61%) of a white solid of compound I-1. ESI-MS M/Z 342 (MH—H$_2$O)$^+$.

Example 2

Synthesis of Compound I-2

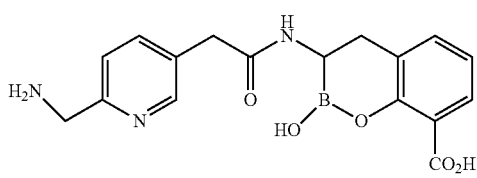

I-2

The compound I-2 is the specific structure of formula (I) when m=1, n=1, Y is 2,5-disubstituted pyridinyl, R1 and R2 are all hydrogen.

Figure 4:
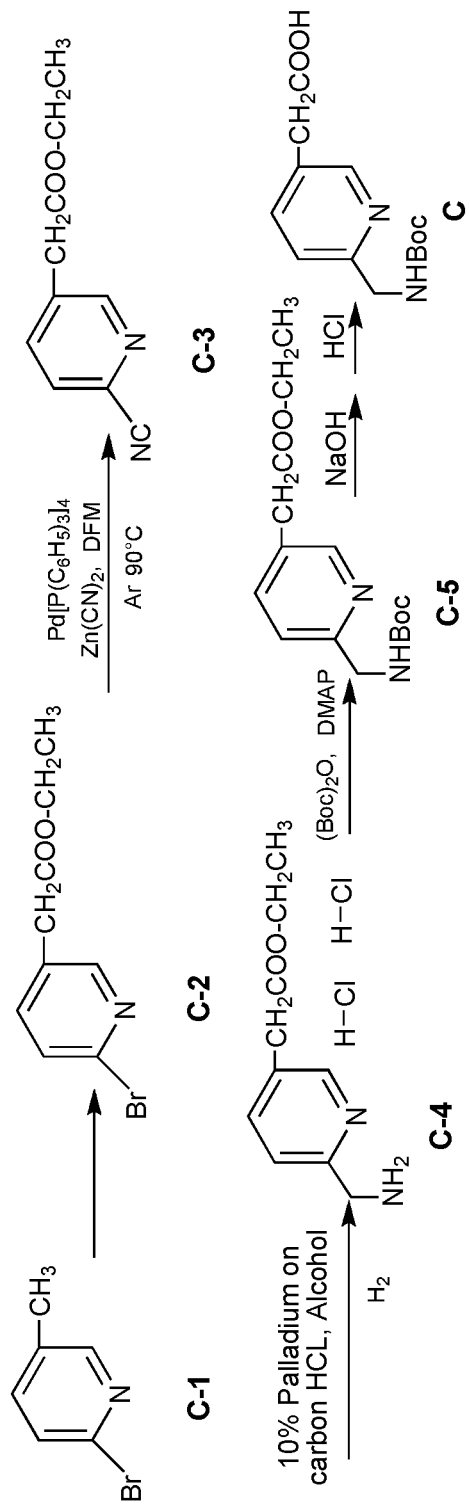
FIG. 4 is a synthetic route of a compound C as described in the disclosure.

I. Synthesis of 6-tert-butoxycarbonyl aminomethyl-pyridine-3-yl-acetic acid, i.e. Compound C, the Synthetic Route is Shown in FIG. 4

Step 1. Synthesis of (6-bromo-pyridine-3-yl)-ethyl acetate (Compound C-2)

In a 500 mL round bottom flask, diisopropylamine (13.2 mL, 93.92 mmol) was mixed with tetrahydrofuran (41 mL) and cooled to −78° C. N-butyllithium (dissolved in 2.5 M hexane; 38 mL, 91.20 mmol) was added and the mixture was stirred for 30 minutes. Then 2-bromo-5-methylpyridine dissolved in 17 mL of tetrahydrofuran (compound C-1.5 ml, 46.92 mmol) was added. The mixture was stirred for 2 hours. Diethyl carbonate (6.2 mL, 51.40 mmol) was then added and the mixture stirred overnight while gradually warming to room temperature. The reaction was quenched with saturated ammonium chloride and extracted three times with ethyl acetate. The combined organic extracts were washed with brine, dried and concentrated. Purification by silica gel chromatography eluting with a gradient of 2/98 (V/V) to 7/93 (V/V) ethyl acetate/hexane gave the product 8.05 g (70%) of compound C-2 as a colorless oil. ESI-MS M/Z 246 (MH)$^+$.

Step 2. Synthesis of (6-cyano-pyridine-3-yl)-ethyl acetate (Compound C-3)

6-bromo-pyridine-3-ethyl acetate (compound C-2, 4.91 g 20.0 mmol), zinc cyanide (9.94 mol), tetra (triphenylphosphine) palladium (0) (4.69 g, 4.06 mmol) and DMF (100 mL) were added to a 300 mL round bottom flask. The mixture was heated under argon at 90° C. for 15 hours. After cooling, the reaction was quenched with 10% ammonium acetate solution and extracted with ethyl acetate. The combined organic extracts were washed with water, brine and concentrated by drying, purified by chromatography on silica gel, eluting with a gradient of 2/98 (v/v) ethyl acetate/hexane to 10/90 (v/v) ethyl acetate/hexane to afford 3.45 g of compound C-3 (90.3%). ESI-MS M/Z 191 (MH)$^+$.

Step 3. Synthesis of (6-aminomethyl-pyridine-3-yl) ethyl acetate dihydrochloride (Compound C-4)

6-cyano-pyridine-3-yl ethyl acetate (compound C-3, 4 g, 21.03 mmol), 10% palladium carbon (2 g), and hydrochloric acid (15.7 mL of 4 M in dioxane) were added to ethanol (140 mL) and loaded into a Parr shaker, followed by charging of 60 psi hydrogen. The mixture was stirred for 4 hours and filtered through Celite and the filtrate was concentrated to give 5.13 g (91%) of the crude compound C-4. ESI-MS M/Z 195 (MH)$^+$.

Step 4. Synthesis of (6-tert-butoxycarbonyl-pyridine-3-yl)-ethyl acetate (Compound C-5)

(6-aminomethyl-pyridine-3-yl)-ethyl acetate dihydrochloride (compound C-4, 5.13 g 19.2 mmol) and di-tert-butyl dicarbonate (12.98 g, 59.5 mmol) were added to 40 mL of unbutanol and 13 mL of acetone, followed by addition of sodium bicarbonate (3.23 g 38.4 mmol) and 4-(dimethylamino) pyridine (5.13 mg, 4.20 mmol). The mixture was stirred overnight at room temperature. The reaction was quenched with saturated ammonium chloride and extracted three times with ethyl acetate. The combined organic extracts were washed with brine, dried and concentrated. The crude material was purified by silica gel chromatography, and eluting with 20/80 (v/v) to 30/70 (v/v) ethyl acetate/hexane gradient gave the product 6.02 g (100%) of compound C-5 as a white solid: ESI-MS M/Z 295 (MH)$^+$.

Step 5. Synthesis of (6-tert-Butoxycarbonyl-aminomethyl-Pyridine-3-yl)-Acetic Acid (Compound C)

To (6-tert-butoxycarbonyl-aminomethyl-pyridine-3-yl) ethyl acetate (compound C-5, 6 g, 20.3 mmol) dissolved in a mixed solution of methanol (20 mL) and water (10 mL), sodium hydroxide (1.05 g, 2.62 mmol) was added. The mixture was stirred for 15 hours. The methanol was removed in vacuo and 3N hydrochloric acid was added dropwise with stirring to give a pH between 4 and 5. After concentrated solution. Purification by means of carbon 18 phase silica gel chromatography gave 5.42 g (100%) of compound C as a white solid: ESI-MS M/Z 267 (MH)$^+$.

Figure 5:
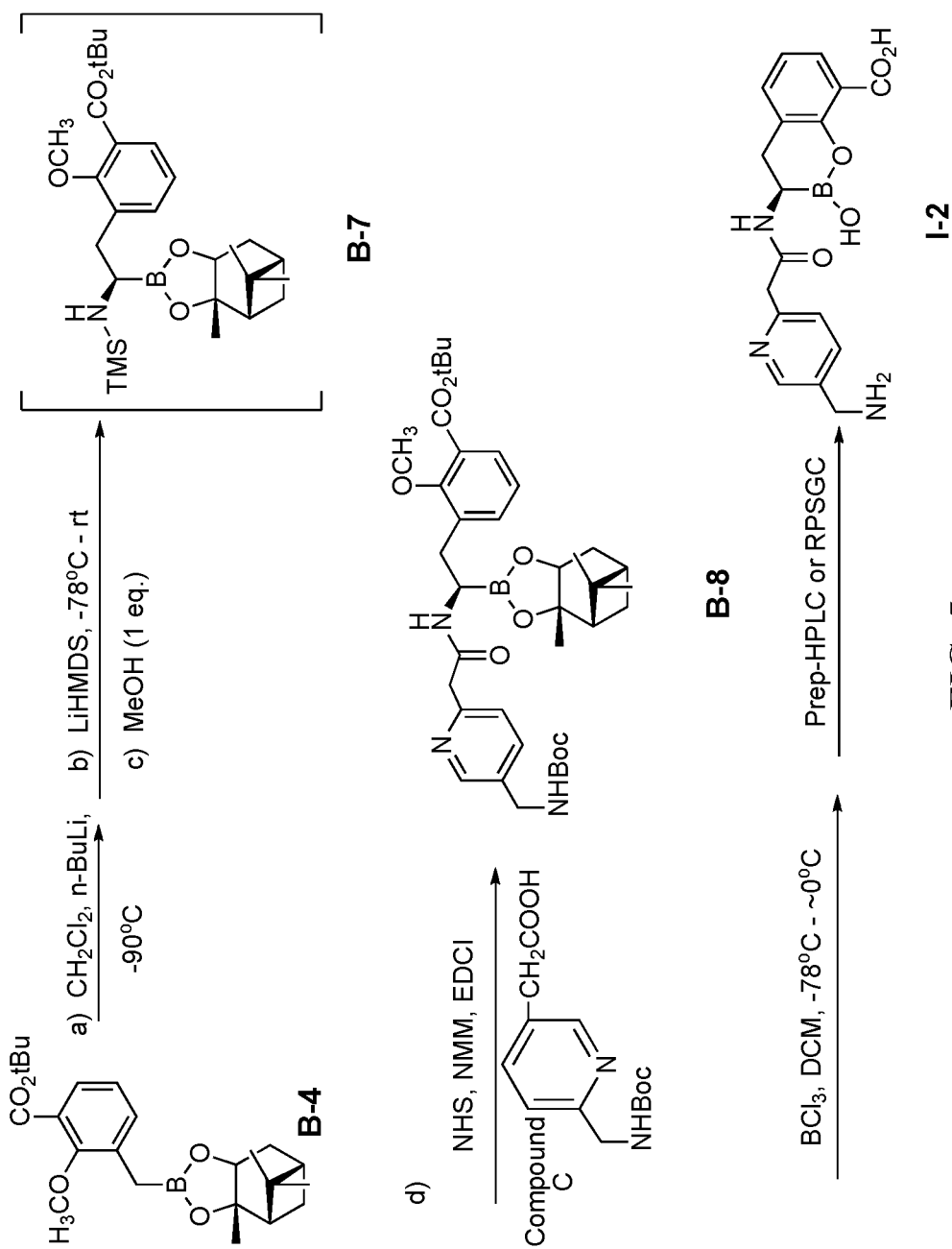
FIG. 5 is a synthetic route of a compound I-2 as described in the disclosure.

II. The Synthetic Route of Compound I-2 is Shown in FIG. 5

Step 1. Synthesis of 3-(2-((5-tert-butoxycarbonyl-pyridine-3-ylacetyl)-amino)-2-(2,9,9-trimethyl-3,5-dioxo-4-tricyclic (6,1,1,0$^{2,\,6}$)-decyl-4-yl-ethyl-2-methoxyl-benzoic acid)-tert-butyl ester (Compound B-8)

N-butyllithium (10.5 mL, 26.3 mmol, dissolved in 2.5 M hexane solution) was added to a mixture of tetrahydrofuran (65 mL) and anhydrous dichloromethane (1.80 mL, 28.50 mmol) at −90° C. for 15 minutes. The solution was stirred at −90° C., and 2-methoxy-3-(2,9,9-trimethyl-3,5-dioxo-4-boro-tricyclic (6,1,0$^{2,6}$)-decyl-4-methyl-isotert-benzoate (compound B-4, 8.77 g, 21.93 mmol) dissolved in THF (11 mL) was added by syringe within 20 minutes. The compound B-4 was prepared in the same manner as in Example 1. After 30 minutes the cold trap was removed and the mixture warmed to 0° C. and stirred for 1 hour. The solution was then cooled to −78° C. and lithium bis (trimethylsilyl) amino (LHMDS, 1.0 M THF solution, 24.1 mL) was added over 5 minutes. The reaction was gradually warmed and stirred overnight. The mixture was then cooled to −10° C. and anhydrous methanol (0.96 mL 24.1 mmol) was added. It was stirred for 45 minutes and then the ice bath was removed and the solution stirred for 1.25 h at room temperature. At this stage LC-MS shows 2-methoxy-3-(2-(2,9, 9-trimethyl-3-5-dioxo-4-boro-tricyclic $(6,1,1,0^{2,\,6})$ decyl-4-yl)-2-(trimethylsilylamino)-ethyl-tert-butylbenzoate (compound B-7) was produced. All solvent was then removed in vacuo and the residue dissolved in 140 mL of DCM for use.

6-tert-butoxycarbonyl aminomethyl-pyridine-3-yl-acetic acid (compound C, 55.84 g, 22.0 mmol)) was dissolved in DCM (220 mL) in a separate dry round bottom flask. The flask was cooled to 0° C. and NMM (7.3 mL, 66.4 mmol), N-hydroxysuccinimide (NHS) (5.09 g, 44.2 mmol), and 1-(3-dimethylaminopropyl)-3-ethylcarbodiimide hydrochloride (EDCI) (8.54 g, 44.2 mmol) were added. The mixture (DCM solution of the compound B-7) was stirred at 0° C. for 30 minutes and then at room temperature for one hour. The DCM solution of the compound B-7 was added to the reaction mixture at 0° C. The cooling bath was removed and the reaction was quenched with water after stirring at room temperature for 1.5 hours. The aqueous phases were extracted with dichloromethane, and the combined organic layers were dried over sodium sulfate and concentrated in vacuo. The crude product was purified by flash column chromatography of silica gel eluting with a 30/70 (v/v) ethyl acetate/hexane gradient to 70/30 (v/v) ethyl acetate/hexane to give 2.84 g (20%) of product compound B-8, yellowish. ESI-MS M/Z 678 (MH)$^+$.

Step 2. Synthesis of (2R)-3-(2-(2-((6-aminomethyl-pyridine-3-yl-acetyl)-amino)-2-hydroxyboronethyl)-2-hydroxy-benzoic acid hydrochloride (Compound I-2)

3-2 ((6-tert-butylamino-picolyl-)-tert-butyl 2,9,9-trimethyl-3,5-dioxa-4-boro-tricyclic $(6,1,1,0^{2,\,6})$ decyl-4-yl)-2-methoxy-benzoic acid (compound B-8, 2.48 g, 3.66 mmol) was dissolved in dichloromethane. Boron trichloride (38 mL, 38 mmol, 1M solution in DCM) was added under argon at −78° C. The mixture was stirred for 1 hour. The reaction was quenched with water (30 mL) at 0° C., evaporated into methylene chloride, and followed by addition of water (20 mL). And the aqueous layer (3 times, 30 mL) was extracted with ether. After aqueous phase concentration, the product was purified by C18 reverse phase silica gel chromatography to give 770 mg (58%) of a white solid compound I-2. ESI-MS M/Z 356 (MH-H$_2$O)$^+$.

Performance Testing of the Compounds Prepared as Described Above as β-Lactamase Inhibitors Experimental Methods for Analysis of β-Lactamases Isolation of beta-lactamases: Crude beta-lactamase extract was prepared from 20 mL of culture shaken overnight. *Escherichia coli* cells containing SHV5 or CTXM15, *Enterobacter cloacae* containing P99, *Klebsiella pneumoniae* containing KPC2, *Escherichia coli* cells containing either SHV5 or CTXM15, *Acinetobacter baumannii* containing oxa-23 and *Pseudomonas aeruginosa* containing vim-2 were diluted 10-fold, and grown at 37° C. in Mueller Hinton II (MHII) broth to logarithmic mid-term (OD at 600 nm, 0.5-0.8). The cells were precipitated at 5000 g, washed and resuspended in 2 mL of PBS at pH 7.0. Beta-lactamases were extracted by four cycles of freezing, thawing and subsequent centrifugation. The activity of β-lactamase in the extract was determined by using the chromogenic cephalosporin cefotizol. The amount of protein in each of the beta-lactamase preparations was determined by a biscinchoninic acid (BCA) experiment. Beta-lactamase inhibition: to determine the level of beta-lactamase inhibition, the compound was diluted in PBS at pH 7.0 to obtain a concentration of 1000 to 5 μm in a microplate. An equal volume of diluted enzyme stock was added and the plates were incubated at 37° C. for 10 minutes. Then, the solution of cefonitrogen as a substrate was dispensed into each well at a final concentration of 100 μm, and the plate Plus384 (high flux microplate spectrophotometer) was used; Molecular Devices Corp., Syvale, Calif., used a dynamic program to immediately read at 486 nm for 10 minutes. The maximum rate of metabolism was then compared to the control well (without inhibitor) and the percentage of enzyme inhibition was calculated for each concentration of inhibitor. The inhibitor concentration (IC$_{50}$) required to reduce the initial hydrolysis rate of the substrate by 50% was calculated using the Software SoftMax Pro 5.0 (Molecular Devices Corp.) at 486 nm as the residual activity of beta-lactamases. The ability of the compound to inhibit beta-lactamase was evaluated using the methods described above. The results of these experiments are summarized in representative enzymes (where SHV-5 and CTXM-15 are different subtypes of ambler class an extended spectrum beta-lactamase, KPC-2 is class a carbapenem enzyme, VIM-2 represents class b metalloenzyme, P99+ represents chromosome class c, where OXA-23 belongs to class D representative enzymes) in FIG. 6, where A represents an IC$_{50}$ of greater than 1 μm, B represents an IC$_{50}$ of 0.1 to 1 μm, and C represents an IC$_{50}$ of less than 0.1 μm.

In Vitro Antibacterial Experiment of Inhibition of β-Lactamase

To determine that ability of the test compound to inhibit the growth of beta-lactamase-producing bacterial strain, traditional cell-based screening experiments were employed. Six bacterial strains producing beta-lactamases were used: *Escherichia coli* expressing class an extended spectrum beta-lactamases (esbl) ctxm15 and shv5 (*E. coli*), *Klebsiella pneumoniae* expressing class a carbapenem enzyme kpc2, *Pseudomonas aeruginosa* expressing class B VIM-2, *Enterobacter cloacae* expressing class C P99+, and *Acinetobacter baumannii* expressing class D OXA-23 were studied. To evaluate the ability of the test compound to inhibit beta-lactamase activity, an improved broth microdilution experiment was used. This experiment was performed in Cation Adjusted Mueller Hinton Broth (CAMHB, BD #212322, BD Diagnostic Systems, Sparks, Md.). The bacterial strains were grown in CAMBH broth for 35 hours. All six strains were grown in the presence of 50 μg/mL ampicillin to ensure that resistance was maintained. At the same time, the test compound was diluted into 0.1 mg/mL stock solution in DMSO. The compound was added to the microplate and diluted in a 2-fold series in CAMHB to a final concentration of 32 to 0.25 μg/mL. A cover layer containing cephalosporin CAMHB was added to the compound at a termination concentration of 8 μg/mL or 16 .m. Ceftazidime (CAZ, Sigma # C38091G, Sigma Aldrich, St. Louis, Mo.) of 8 μg/mL was used as a partner antibiotic for the following strains: *Escherichia coli* expressing class A ESBL SHV5 (MIC alone >1024 μg/mL), *Klebsiella pneumoniae* (MIC=32 μg/mL) expressing carbapenem class A KPC2 and *Enterobacter cloacae* (MIC=256 μg/mL) expressing class C P99+AmpC; Ceftazidime 16 μg/mL (CAZ) was used as a partner of the following strains: *Acinetobacter baumannii* expressing class D enzyme OXA-23 (MIC>256 μg/mL), *Pseudomonas aeruginosa* expressing class B enzyme VIM-2 (MIC>256 μg/mL); And 8 μg/mL cefotaxime (TAX, USP #1097909, U.S. Pharmacopeia, Rockville, Md.) was used as a co-antibiotic for *E. coli* expressing class A ESBLCTXM15 (MIC=1024 µg/mL). The MIC reading of the dose escalation test of the test compound indicates the concentration of the analyte sufficient to inhibit beta-lactamase activity and protect the original antibacterial activity of cephalosporins. Six plates are required for each compound and each plate is used for one bacterial strain. In addition to the dose escalation test of the test compound, the MIC of a group of cephalosporins was tested to ensure that the strain remained consistent in behavior between the test and the test. Once the test compound and cephalosporin are added, the plates may be inoculated. The inoculation was carried out according to the CLSI broth microdilution method. After inoculation, the plates were incubated at 37° C. for 16-20 hours and then the minimum inhibitory concentration (MIC) of the test compound was determined. The ability of the compound to inhibit the growth of beta-lactamase producing bacteria in the presence of beta-lactam antibiotics was evaluated using the methods described above. The results are shown in FIG. 7, where A represents MIC>16 µg/mL, B represents MIC=2-16 µg/mL, and C represents MIC<1 µg/mL.

It will be obvious to those skilled in the art that changes and modifications may be made, and therefore, the aim in the appended claims is to cover all such changes and modifications.

What is claimed is:

1. A compound having a formula of:

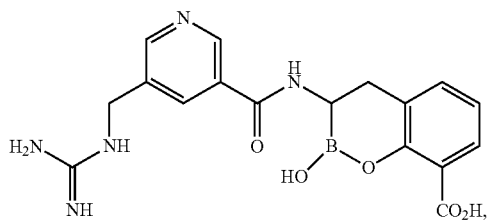

I-9

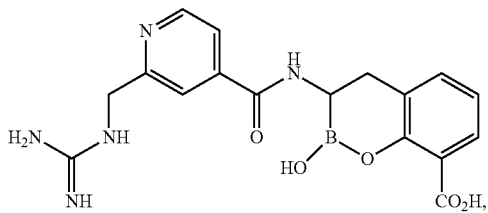

I-10

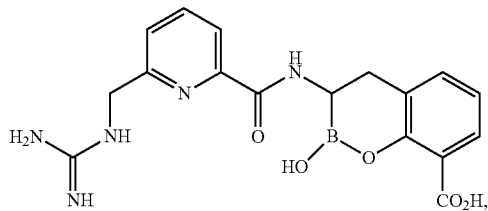

I-11

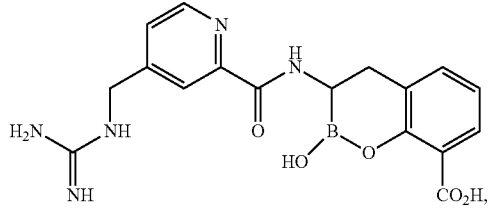

I-12

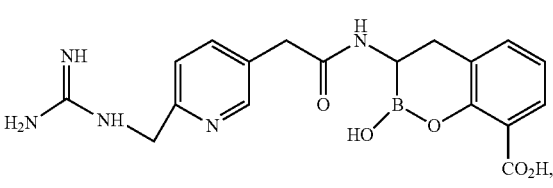

I-13

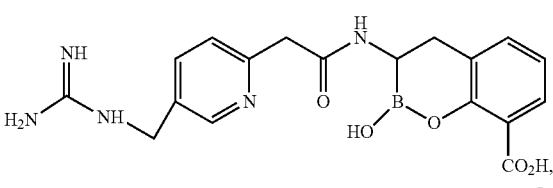

I-14

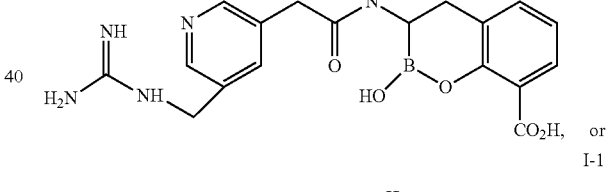

I-15

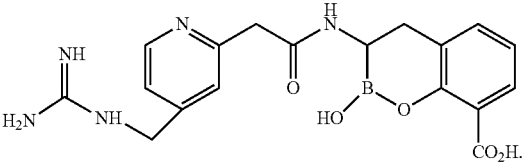

I-16, or

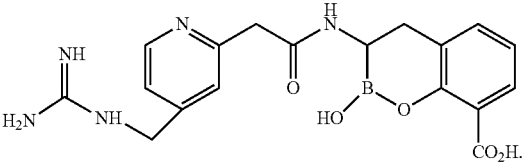

* * * * *